United States Patent [19]

Gau et al.

[11] 4,299,118
[45] Nov. 10, 1981

[54] VISCOMETER

[75] Inventors: Gerald S. Gau, Houston; David E. Cain, The Woodlands, both of Tex.

[73] Assignee: Halliburton Services, Duncan, Okla.

[21] Appl. No.: 95,589

[22] Filed: Nov. 19, 1979

[51] Int. Cl.³ .......................................... G01N 11/14
[52] U.S. Cl. .......................................... 73/59; 73/60
[58] Field of Search ................................. 73/59, 60

[56] References Cited

U.S. PATENT DOCUMENTS

| | | | |
|---|---|---|---|
| 2,703,006 | 3/1955 | Savins | 73/59 |
| 3,327,825 | 6/1967 | Fann | 192/104 |
| 3,435,666 | 4/1969 | Fann . | |
| 3,514,685 | 5/1970 | Burgess . | |
| 3,803,903 | 4/1974 | Lin | 73/59 |
| 3,935,726 | 2/1976 | Heinz . | |
| 4,062,225 | 12/1977 | Murphy et al. | 73/60 |
| 4,148,216 | 4/1979 | Do et al. | 73/59 |
| 4,184,364 | 1/1980 | Du Bae . | |
| 4,214,475 | 7/1980 | Carter et al. | 73/59 |

FOREIGN PATENT DOCUMENTS

| | | | |
|---|---|---|---|
| 81265 | 5/1895 | Fed. Rep. of Germany | 73/59 |
| 1245183 | 9/1971 | United Kingdom . | |

*Primary Examiner*—James J. Gill

*Attorney, Agent, or Firm*—John H. Tregoning; Thomas R. Weaver; Lucian Wayne Beavers

[57] ABSTRACT

An improved rotational viscometer is provided, having a base, a housing, and one and only one adjustable support leg supporting the housing from the base. The support leg provides for adjustment of the length of the leg and provides for alignment of the housing relative to the base. A rotatable tubular sleeve extends downwardly from the housing, and an electric motor is provided in the housing for driving the rotatable sleeve. The electric motor is connected to the rotatable sleeve by a toothed pulley and belt assembly. A cylindrical non-metallic bob is concentrically positioned within the tubular sleeve and is attached to the lower end of a bob shaft. The upper end of the bob shaft has an indicator dial attached thereto and is connected to the housing by a torsional string. An improved motor control system for the viscometer is provided which allows the viscometer to be powered by several alternative power sources and which provides an internal safety shut off of the power to the electric motor in a situation where the rotating tubular sleeve becomes jammed. Also provided is an illumination light for the indicator dial which varies in intensity depending upon whether the electric motor is rotating at one of a plurality of selectable nominal motor speeds.

36 Claims, 7 Drawing Figures

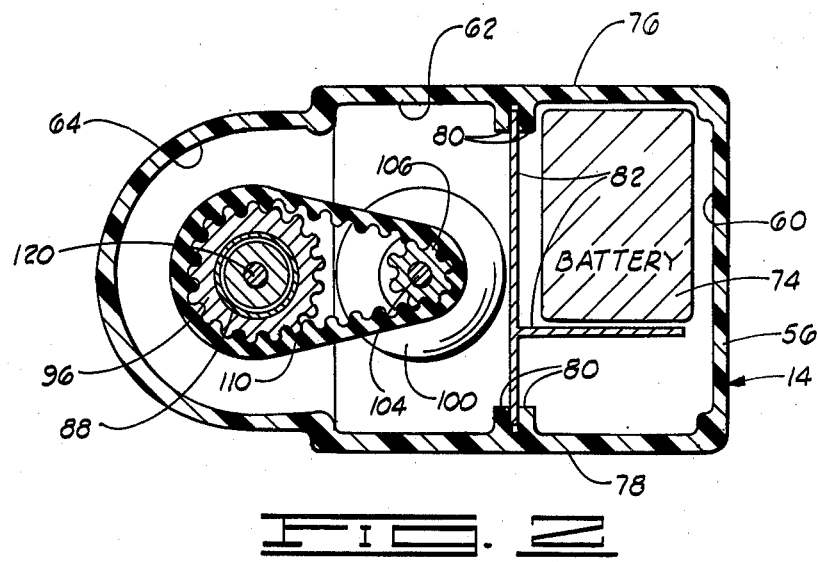
FIG. 2
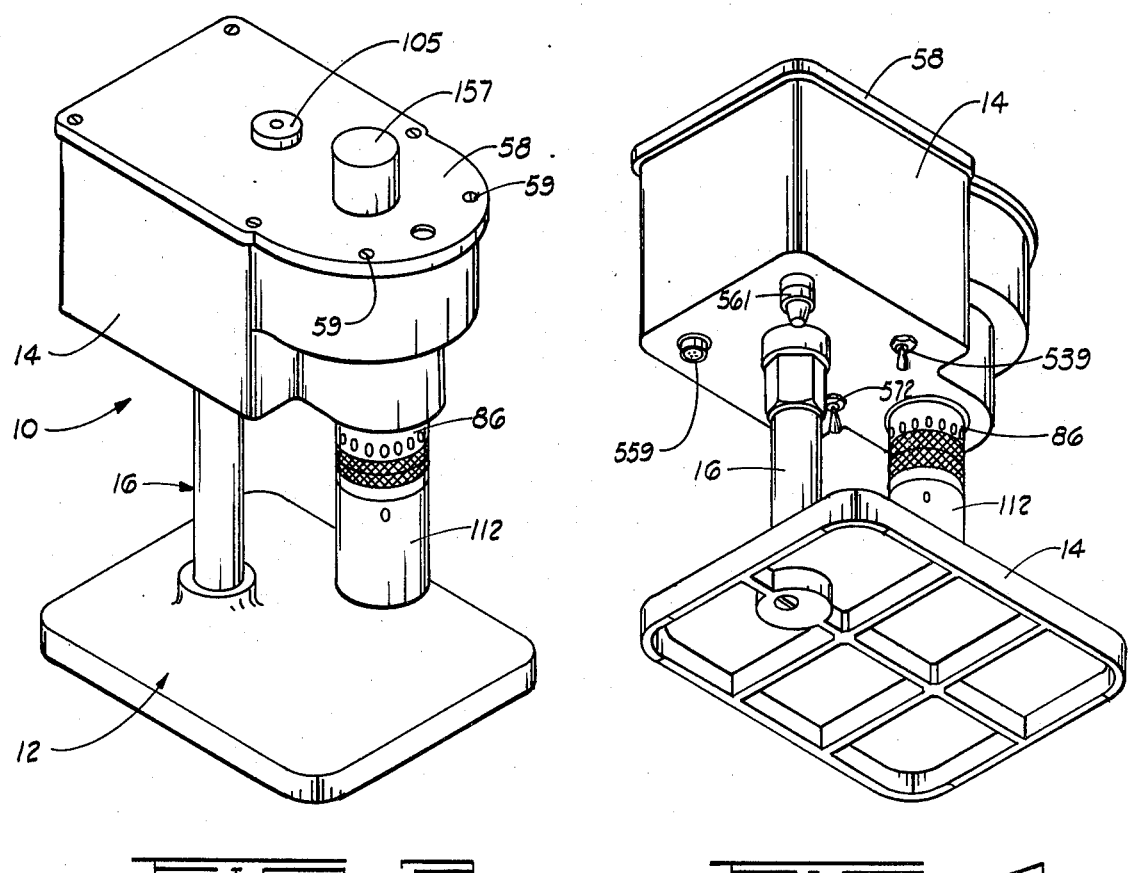
FIG. 3
FIG. 4

VISCOMETER

The present invention relates generally to viscometers, and more particularly, but not by way of limitation, to viscometers adapted for the measurement of viscosity, yield point, and gel strength of mud mixtures for use in well drilling operations.

The prior art includes numerous viscometers of the type having a base, a housing, a support means for supporting the housing from the base, a rotatable tubular sleeve extending downwardly from the housing, means for rotating the sleeve, a cylindrical bob positioned with respect to the sleeve such that rotation of the sleeve within a liquid will rotate the liquid and thereby impart a viscous drag to the bob, means including a spring for imparting a torque to the bob proportional to the deflection of the bob from a zero position, and means for measuring the deflection of the bob from said zero position.

Two examples of such prior art viscometers are shown in U.S. Pat. No. 3,327,825 to Fann and No. 2,703,006 to Savins.

The present invention provides numerous improvements over devices such as those of Fann and Savins.

An improved support means is provided for supporting the housing from the base. This support means includes one and only one support leg which has adjustment means for adjusting a length of the support leg and alignment means for maintaining the rotating tubular sleeve of the viscometer over a fixed position on the base of the viscometer.

The drive means of the present invention, for rotating the sleeve of the viscometer, includes a resilient toothed endless belt connected between toothed pulleys attached to an electric motor and to the rotating sleeve. Such a drive system provides for a positive, accurate transmission of rotational speed from the motor to the sleeve, and at the same time, provides damping in the drive system for eliminating vibration therefrom.

An improved power supply and motor control system is provided which permits power to be obtained from several alternative sources and which provides a safety shut off feature in the event the rotating sleeve of the viscometer should become jammed.

Other improvements provided by the present invention include a non-metallic bob located within the rotating sleeve and a snap on removable plastic cover for protection of the calibration adjustment means of the viscometer.

Numerous features and advantages of the present invention will be readily apparent to those skilled in the art upon a reading of the following disclosure in conjunction with the accompanying drawings.

FIG. 2 is a sectional view taken about line 2—2 of FIG. 1.

FIG. 3 is an isometric view of the viscometer of FIG. 1 as viewed from above.

FIG. 4 is an isometric view of the viscometer of FIG. 1 as viewed from below.

FIG. 5 is a preferred embodiment schematic circuit diagram of the speed detecting means of the viscometer of FIG. 1.

Figure 1:
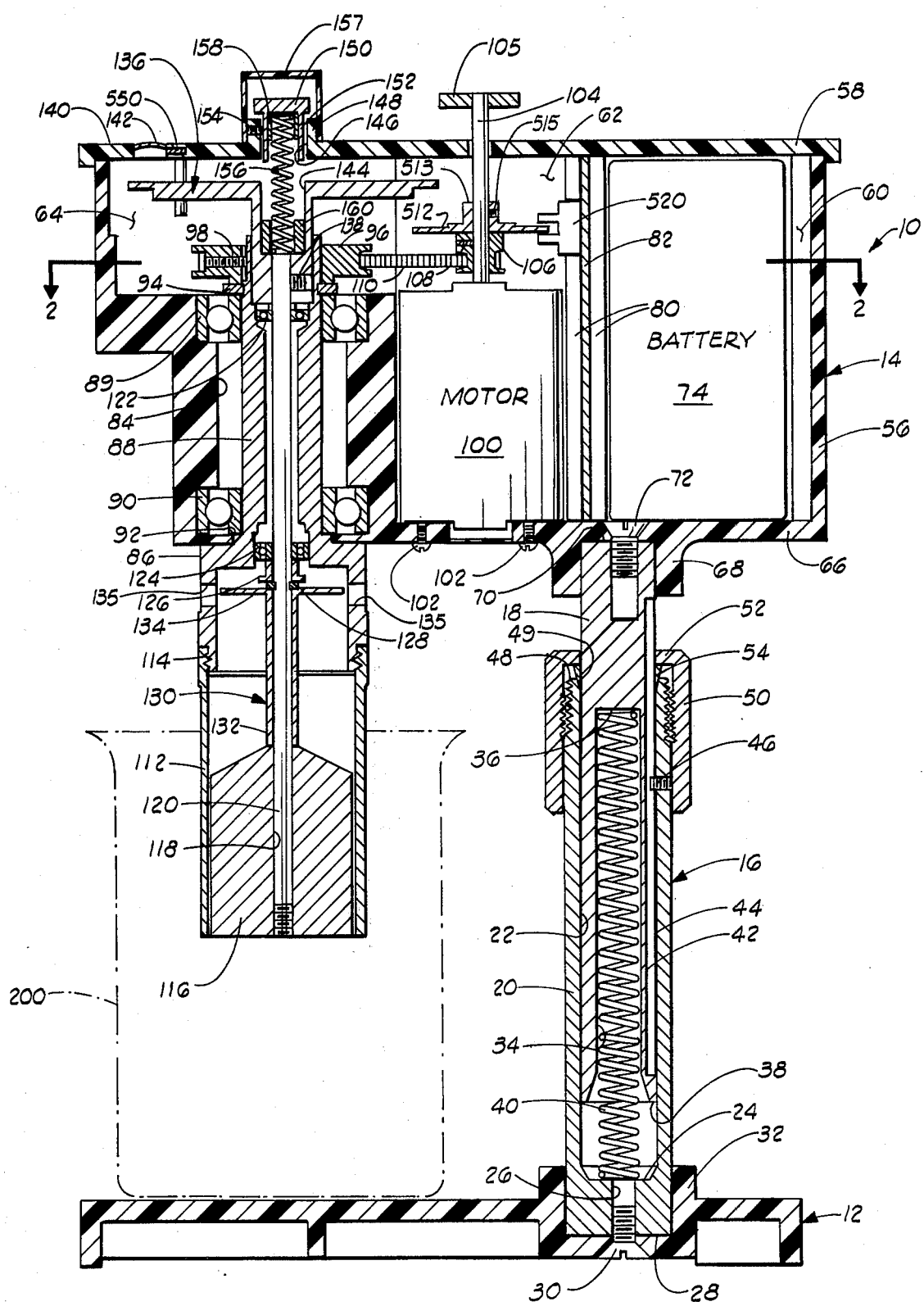
FIG. 1 is an elevation sectional view of the viscometer of the present invention.

Referring now to the drawings, and particularly to FIG. 1, the viscometer of the present invention is shown and generally designated by the numeral 10. The viscometer 10 includes a base 12, a housing 14, and a support leg 16 for supporting housing 14 from base 12.

The support leg 16 may generally be referred to as a support means and it is noted that there is one and only one leg comprising the support means 16.

Support leg 16 includes an upper leg member 18 and a lower leg member 20. Upper leg member 18 is telescopingly received within an inner bore 22 of lower leg member 20. Inner bore 22 has a blind lower end 24. A threaded smaller bore 26 communicates blind end 24 with lower end 28 of lower leg member 20. A flat head machine screw 30 connects lower leg member 20 to base 12. The lower end 28 of lower leg member 20 is closely received within a receiving cup 32 of base member 12.

Upper leg member 18 includes a bore 34 having a blind upper end 36 and being open at lower end 38 of upper leg member 18.

A coil type compression spring 40 is received within bore 34 of upper leg member 18 and has its upper and lower ends engaging blind end 36 of bore 34 and blind end 24 of bore 22, respectively.

Upper leg member 18 includes an axial slot 42 disposed in cylindrical outer surface 44 thereof. Lower leg member 20 includes a radially inward projecting pin 46 which is attached to lower leg member 20 and protrudes radially inward into engagement with axial slot 42 of upper leg member 18 so as to allow relative axial motion between upper and lower leg members 18 and 20, but to prevent relative rotational movement therebetween. The pin 46 and slot 42 may generally be referred to as an alignment means for maintaining the relative location of the housing 14 and components attached thereto over the base 12.

Threadedly attached to an upper end 48 of lower leg member 20 is collar means 50 which includes a radially inward projecting shoulder 52.

Shoulder 52 engages an upper end of an annular packing gland means 54. Packing gland means 54 is a means for wedging between upper and lower leg member 18 and 20 to prevent relative axial motion therebetween. Packing gland means 54 is wedge shape in cross-section, and engages a beveled inner edge 49 at the upper end of bore 22 of lower leg member 20.

When the collar means 50 is turned so as to tighten the theaded connection with lower leg member 20, the annular packing gland 54 is forced downward and wedged between upper and lower leg members 18 and 20 so as to lock them together. The collar means 50 and packing gland 54 may generally be referred to as a releasable locking means for selectively fixing upper leg member 18 relative to lower leg member 20 and releasing upper leg member 18 from lower leg member 20.

The spring biasing means 40 connected between upper and lower leg members 18 and 20, biases upper leg member 18 upwards relative to lower leg member 20, so that it may be said to bias the telescoping upper and lower leg members 18 and 20 toward an extended position.

The length of support leg 16 is adjusted by loosening the collar 50 and telescoping upper leg member 18 within lower leg member 20 to the desired position. Then the collar means 50 is tightened so as to lock the upper and lower leg members together.

The housing 14 is a non-metallic housing comprising a main housing section 56 the top of which is covered by a housing cover 58. Housing cover 58 is attached to main housing section 56 by a plurality of suitable fastening screws 59 (See FIG. 3).

Main housing section 56 includes a battery and power supply receiving compartment 60, a motor receiving compartment 62, and a rotor receiving compartment 64.

A bottom 66 of main housing section 56 includes a downwardly extending receiving cup 68 which closely receives an upper end 70 of upper leg member 18. Upper leg member 18 is connected to bottom 66 by a flat head machine screw 72.

Located within battery receiving compartment 60 is a battery 74 which may also be referred to as an internal direct current source.

As is best seen in FIG. 2, sidewalls 76 and 78 of main housing section 56 each include a pair of inwardly extending spaced flanges 80. Held between the flanges 80 and separating the compartments 60 and 62 is a circuit board 82. Circuit board 82 holds the electronic control circuitry which is described in detail below.

Rotor receiving compartment 64 includes a vertical cylindrical bore 84 in the lower portion thereof. A rotor 86 includes a cylindrical rotor shaft 88 which is rotatingly mounted within cylindrical bore 84 by upper and lower rotor bearings 89 and 90, respectively. An upward facing annular shoulder 92 of rotor 86 engages a lower surface of lower rotor bearing 90, and a rotor snap ring 94 is received within an annular groove in rotor shaft 88 above upper rotor bearing 89 so as to vertically fix rotor 86 in place relative to housing 14.

A rotor pulley 96, which may also be referred to as a driven pulley, is fixedly attached to rotor shaft 88 by set screw 98.

An electric motor or drive means 100 is located in motor receiving compartment 62 and attached to bottom 66 of main housing section 56 by a plurality of suitable fastening screws 102. Extending from motor 100 is a rotating motor shaft 104. Attached to the upper end of motor shaft 104 is a motor shaft knob 105 which allows motor shaft 104 to be rotated by hand.

A drive pulley 106 is fixedly attached to motor shaft 104 by a set screw 108.

Connected between drive pulley 106 and rotor shaft pulley 96 is a resilient toothed endless belt 110.

Drive belt 110 is preferably constructed of urethane. The toothed urethane drive belt 110 provides precise timing accuracy at high speeds, and additionally, its resilient properties provide a degree of damping in the drive system which helps to reduce vibration of the rotor 86.

A rotating tubular sleeve 112 is attached to a lower end of rotor 86 at threaded connection 114.

Located concentrically within sleeve 112 is a bob 116. The bob 116 is preferably constructed of a non-metallic material such as polyvinyl chloride. Bob 116 is of substantially solid construction except for a central bore 118 therethrough, within which is threadedly received a bob shaft 120. Prior art bobs have generally been constructed as a hollow metallic member such as the bob shown in U.S. Pat. No. 2,703,006 to Savins. Also, there have been substantially solid bobs constructed of metallic materials such as brass or stainless steel.

A number of advantages are realized by the use of a substantially solid non-metallic bob such as bob 116. The non-metallic material, such as a polyvinyl chloride, has a lower specific heat and lower thermal conductivity, so that when the bob 116 is immersed in a sample of the fluid to be tested, very little heat is absorbed from or transferred to the fluid from bob 116 so that relatively little time is required for the sample to reach thermal equilibrium thereby permitting an accurate test to be conducted.

Additionally, the non-metallic bob 116 is non-corrosive. The non-metallic bob 116 accepts surface finishes comparable to those previously applied to standard metallic bobs so that the surface properties of the non-metallic bob 116 are comparable to prior art metallic bobs.

Also, the non-metallic bob 116 is relatively light in weight and therefore does not load the bearings as heavily as a solid metallic unit would.

The bob shaft 120 is rotatingly mounted within rotor 86 by upper and lower bob shaft bearings 122 and 24, respectively. Located below lower bob shaft bearing 124 is a bob shaft spacer 126 which is held in place by a snap ring 128. Located below snap ring 128 is a dust shield 130 which includes a cylindrical portion 132 disposed around bob shaft 120 and a circular plate portion 134 at the upper end of cylindrical portion 132 for shielding those components above upper plate portion 134 from the test fluid which tends to be thrown about by rotation of sleeve 112. Circular plate portion 132 also diverts the flow of corrosive gases, such as hydrogen sulfide, out the vent holes 135 in the side of rotor 86.

An indicator dial assembly 136 is attached to the upper end of bob shaft 120 by set screw 138. A plurality of dial indicia (not shown) are located upon the top surface 140 of indicator dial 136 and may be viewed through lens 142 disposed in housing cover 58 so that a rotational deflection of bob 116 relative to housing 14 may be observed. A light emitting element 550, described in detail below, is provided adjacent lens 142 for illuminating the indicator dial assembly 136.

Indicator dial assembly 136 includes a cylindrical bore 144 in the upper end thereof.

Cover 58 of housing 14 includes a calibration opening 146 about which is concentrically disposed an upward projecting annular shoulder 148.

A calibration knob 150 includes a downward extending cylindrical calibration sleeve portion 152 which is received in calibration opening 146. Calibration knob 150 may be fixed relative to shoulder 148 by set screw 154 disposed through shoulder 148 and engaging calibration sleeve 152.

A snap on protective plastic cover 157 snaps over shoulder 148 so as to cover calibration knob 150 during the normal operation of viscometer 10 to prevent inadvertent engagement of calibration knob 150 which might change the calibration of viscometer 10.

A coil torsion spring 156 has an upper end tightly engaged with calibration sleeve 152 by an annular split compression sleeve 158. Compression sleeve 158 is an annular member with a vertical split in a portion thereof which permits sleeve 158 to be compressed as it is forced into the inner bore of calibration sleeve 152. This compression of sleeve 158 causes it to tightly grip the upper end of coil spring 156 while at the same time it is caused to tightly engage the inner bore of calibration sleeve 152.

Similarly, the lower end of spring 156 is snugly connected to inner bore 144 of indicator dial assembly 136 by a second annular split compression sleeve 160.

The viscometer 10 also includes control means for controlling the speed of motor 100. This control means allows the speed at which motor 100 rotates the sleeve 112 to be nominally selected and thereafter maintained.

Generally, the control means includes a means for detecting the speed of rotation of the drive means 100 and means for comparing the detected speed of rotation to a selectable one of a plurality of speed reference levels and for altering the speed of rotation in correspondence with the resulting comparison between the detected speed and the selected reference level. Additionally, the control means includes means for stopping the energization of the drive means 100 in response to the detecting means detecting a zero speed of rotation of the drive means 100. The control means also includes a power supply circuit having an internal direct current source. The control means may further include means for adjusting the magnitude of the output of a means for indicating the relative speed of the drive means 100.

Figure 7:
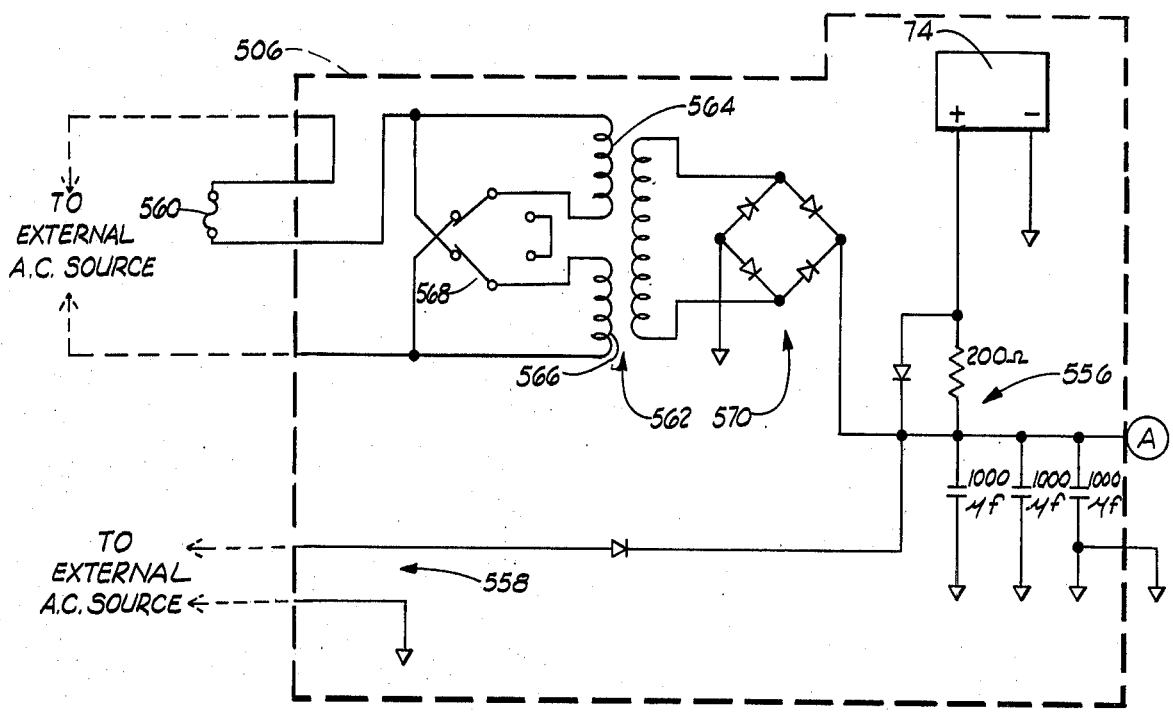
FIG. 7 is a preferred embodiment schematic circuit diagram of the power supply circuit of the viscometer of FIG. 1.
Figure 9:
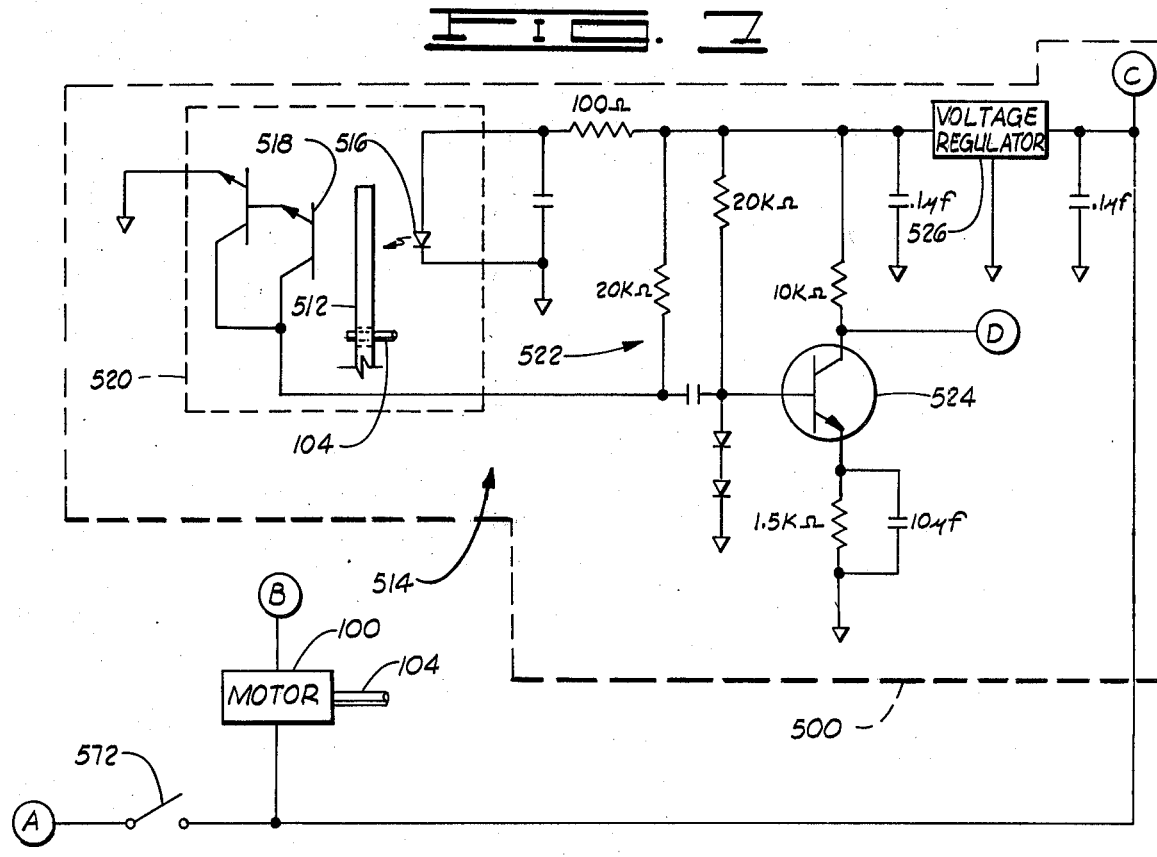
Figure 6:
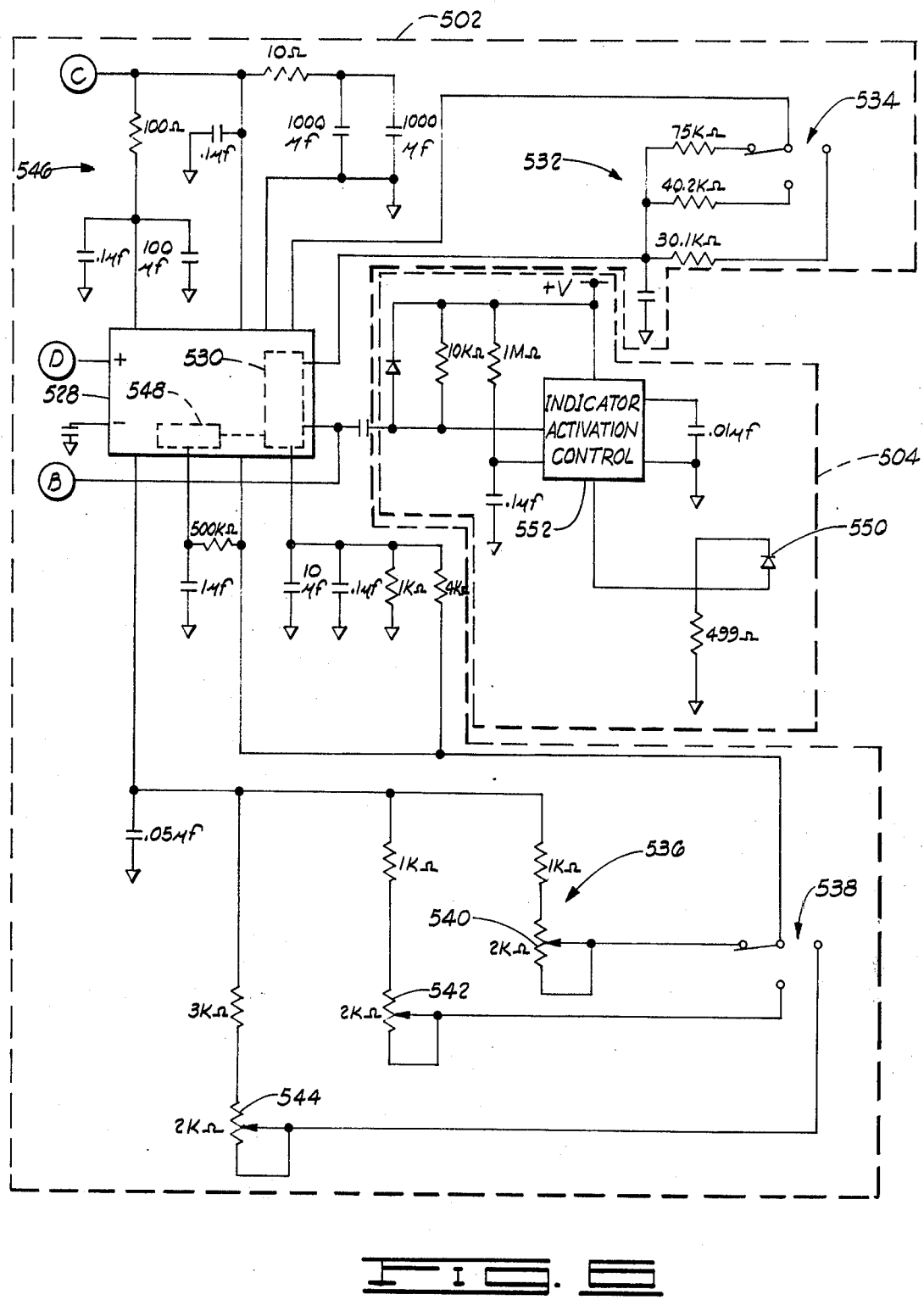
FIG. 6 is a preferred embodiment schematic circuit diagram of the motor activating and deactivating means and the relative speed indicator adjusting means of the viscometer of FIG. 1.

With reference now to FIGS. 5-7, the control means for controlling the speed of the drive means will be described. In particular, when the drive means is a motor such as motor 100, the control means is an apparatus for controlling the speed of rotation of the drive shaft 104 of the motor (and thus also the speed of rotation of the sleeve which is coupled to the drive shaft by the belt). This apparatus variably sets the speed of rotation of the drive shaft 104 of the motor 100, then maintains the speed at that one selected speed.

The control apparatus includes means for detecting the speed of rotation of the drive shaft 104 of the motor 100 and, in the preferred embodiment shown in FIG. 5, for converting that speed into a proportional electrical signal. This detecting means is indicated by the reference numeral 500. FIG. 6 discloses that the control apparatus also includes means for alternatingly activating and deactivating the motor 100 so the speed of the drive shaft 104 is controlled. This means is generally referred to by the reference numeral 502. FIG. 6 also shows that the control apparatus includes means for adjusting the magnitude of the output of a means for indicating the relative speed of rotation of the drive shaft 104 for any one selected speed. This means is generally referred to by the reference numeral 504. The control means further includes a power supply circuit 506 as shown in FIG. 7.

Referring now to FIG. 5, the preferred embodiment circuit diagram of the detecting means 500 will be described. Initially, it will be assumed that the drive means of the viscometer apparatus is the motor 100 having the drive shaft 104 rotated thereby. As schematically illustrated in FIG. 5, connected to this drive shaft 104 is a rotatable member 512 which forms a first part of the detecting means 500. In the preferred embodiment the rotatable member 512 includes a plurality of alternatingly disposed light-passing and light-occluding elements. For example, the light-passing elements may be transparent plastic sections, whereas the light-occluding elements may be opaque plastic sections.

Forming a second part of the detecting means 500 is a means for generating a series of electrical pulses in response to the rotation of the rotatable member 512. This generating means is referred to in FIG. 5 by the reference numeral 514. The generating means 514 has a light-transmitting element and a light-receiving element disposed on opposite sides of the rotatable member 512 so that the light-passing and light-occluding elements pass between the light-transmitting element and the light-receiving element as the rotatable member rotates. In particular, FIG. 5 indicates that the light-transmitting element is a light emitting diode 516 and that the light-receiving element is a photosensitive transistor 518. The light-emitting diode 516 is spaced from the transistor 518 so that the rotatable member 512 can pass therebetween as it rotates. In particular, the light-emitting diode 516 and the transistor 518 may compromise the primary elements of a device 520 such as a Monsanto MCA8 or MCA81 slotted optical limit switch.

Referring to FIG. 1, the rotatable member 512 is shown as a rotatable disk 512 mounted upon a hub 513 which is fixedly attached to drive shaft 104 by set screw 515. The device 520, which contains light emitting diode 516 and transistor 518, is schematically illustrated in FIG. 1 and is mounted on circuit board 82.

In addition to including the light emitting diode 516 and the transistor 518, the generating means 514 may include a number of other components such as a network 522 of resistors, capacitors and diodes and a second transistor 524 as shown in the figure. Additionally, the generating means may include a voltage regulator 526 for providing a regulated voltage level to the remainder of the detecting means 500 circuit.

These constituent members of the detecting means 500 are connected as shown in FIG. 5, so that a series of electrical pulses proportional to the speed of rotation of the drive shaft 104, as detected by the interaction between the rotatable member 512 and the light emitting diode 516 and the photosensitive transistor 518, is produced at the collector of the second transistor 524. This output is indicated by the balloon containing the letter "D". The proportional relationship between the number of pulses produced and the speed of rotation of the drive shaft is determined by the number of alternatingly disposed light-passing and light-occluding elements within the rotatable member 512.

Referring now to FIG. 6, the activating and deactivating means 502 will be described. The activating and deactivating means 502 is responsive to the series of electrical pulses provided by the detecting means 500 as indicated by the balloon containing the letter "D" representing the connection of the activating and deactivating means 502 to the detecting means 500. This connection from the detecting means 500 is made, in the preferred embodiment, to the appropriate input of a motor speed control integrated circuit device such as a Fairchild μA7391 integrated circuit. This is represented in FIG. 6 as the element 528. In the preferred embodiment the element 528 includes means for comparing the magnitudes of a first electrical signal and a second electrical signal, both of which electrical signals are related to the series of electrical pulses proportional to the speed of rotation as provided by the detecting means 500 and for providing a third electrical signal proportional to the comparison of the first and second signals. This means is generally indicated by the reference numeral 530 as shown in FIG. 6.

For establishing the first electrical signal which is to be compared, there is included within the activating and deactivating means 502 a resistor-capacitor network 532 which is switchably connected to a first input of the comparing means 530. The resistor-capacitor network 532 includes a first switch means 534 for interconnecting the resistor-capacitor components into a selectable one of a plurality of combinations to thereby establish the previously mentioned first electrical comparison signal. In the preferred embodiment shown in FIG. 6 the switch means 534 can connect any one of the three resistors shown therein within the operating circuit of the element 528. By appropriately manipulating the switch means 534 any one of three resistor-capacitor combinations, each having a different time constant, can be connected to the input of the comparing means 530 to provide thereto a signal related to the series of electrical pulses.

For establishing the second electrical signal related to the series of electrical pulses, FIG. 6 indicates there is a resistor network 536 having a second switch means 538 for connecting respective ones of the resistors in the resistor network to a second input of the comparing means 530. Included within the resistor network 536 is a plurality of variable resistors. In the FIG. 6 preferred embodiment there are three such variable resistors as indicated by the reference numerals 540, 542 and 544. Each of these variable resistors may be set to provide a predetermined speed reference level to the comparing means 530. Thus, by moving the switch means 538 from one position to the next, a respective one of the variable resistors may be connected to the second input of the comparing means 530 so that the nominal speed at which the motor is to be operated can thereby be set. It is to be noted that the first switch means 534 and the second switch means 538 are synchronously operated in the preferred embodiment so that a respective one of the resistor-capacitor combinations provided by the resistor-capacitor network 532 is connected to the first input of the comparing means 530 when a respective one of the variable resistors within the resistor network 536 is connected to the second input of the comparing means 530. That is, the switch means 534 and 538 are manipulated to maintain a predetermined correspondence between respective ones of the variable resistors within the resistor network 536 and respective ones of the plurality of resistor-capacitor combinations provided by the resistor-capacitor network 532. In the preferred embodiment, this synchronous manipulation is effected by toggling a single toggle lever 539 (shown in FIG. 4) which is mechanically connected to the two switch means 534 and 538 to thereby form the speed switch of the present invention.

Once the comparing means 530 has compared the appropriate comparison signals provided by the resistor-capacitor network 532 and the resistor network 536, it provides an output signal which is connected to the motor 100 as indicated by the balloons containing the letters "B" therein. By so connecting the output to the motor 100, the motor 100 is periodically activated and deactivated as determined by the comparison between the first and second signals provided at the inputs of the comparing means 530 so that the speed thereof is maintained at the nominal speed indicated by the setting of the second switch means 538. Thus, the element 530, the resistor-capacitor network 532 and the resistor network 536 provide means for comparing the detected speed of rotation to a selected one of a plurality of speed reference levels and for altering the speed of rotation in correspondence with the comparison of the detected speed and the selected reference level.

In addition to including the element 530, the resistor-capacitor network 532 and the resistor network 536, the activating and deactivating means 502 includes means for stopping the activation, or energization, of the motor 100 in response to the cessation of the generation of the series of electrical pulses by the generating means 514. That is, when the drive shaft 104 of the motor 100 is not rotating even though the motor 100 is still being energized (such as when the sleeve 112 being driven by the motor 100 is jammed), the present invention includes means for de-energizing the motor 100 at that time so it will not be damaged. This means is referred to in FIG. 6 by the reference numeral 548. For example, this may be a timer which, when it receives no input to indicate that the drive shaft 104 is no longer rotating, causes the output from the element 530 to be such that it de-energizes the motor 100.

FIG. 6 also shows a preferred embodiment schematic circuit for implementing the indicator adjusting means 504. The indicator itself is, in the preferred embodiment, an indicating light 550, such as a light emitting diode. To control the intensity of the illumination of the light emitting diode 550, there is an indicator activation control means 552, such as an integrated circuit timer. Connected to the indicator activation control timer 552 is a plurality of resistors and capacitors as is known in the art to establish the duration of the output pulses provided by the timer 552 in response to an activation signal received from the activating and deactivating means 502. This activation signal is the same one that is provided to control the activation and deactivation of motor 100. In response to the electrical signal provided by the element 530, the timer 552 provides a pulsed output which varies the magnitude of the light emitting diode 550 in accordance with the frequency at which this pulsed output is provided. The frequency is dependent upon the comparison by the element 530 of the actual speed of rotation of the drive shaft to the nominal speed selected by the switch means 538. There is thereby provided means for adjusting the magnitude of the output of the indicating means 550 for indicating the relative speed of rotation of the drive shaft for any one particular setting of the second switch means 538. When the indicating means is the indicating light 550, the light 550 not only indicates the relative speed, but also provides illumination to the dial 136 as shown in FIG. 1 by the relative locations of the light 550 and the dial 136.

With reference now to FIG. 7, the preferred embodiment of the power supply circuit 506 will be described. As FIG. 7 indicates, the power supply circuit includes the internal direct current source 74, such as a 12-volt battery. Being an internal power supply, the battery 74 is contained within the housing 14 containing the remainder of the motor speed control means. The battery 74 is connected to the remainder of the control means circuit and to the motor 100 as indicated by the balloon containing the letter "A". This connection is made through a resistor and a plurality of filter capacitors denoted by the reference numeral 556.

In addition to including an internal direct current source, the power supply circuit of the present invention may include means for connecting an external direct current source, such as the battery of a motor vehicle, to the power supply circuit. This is accomplished in the preferred embodiment through the electrical leads 558 as shown in FIG. 7. The leads 558 connect the respective external direct current source jacks of a power connector 559 (shown in FIG. 4) to the remainder of the power supply circuit.

The power supply circuit may also include means for connecting, via the power connector 559 in the preferred embodiment, an external alternating current source to the power supply circuit. FIG. 7 shows that the alternating current source is connected through a fuse 560 mounted in a fuse housing 561 (as shown in FIG. 4) to a transformer 562. The transformer 562 includes a primary winding having a first subwinding 564 and a second subwinding 566. These subwindings are connected, as shown in FIG. 7, to the external alternating current source and to a switch means 568 so that when the external alternating current source has a first predetermined nominal voltage rating, such as 110 VAC, the switch means 568 is positioned to connect the subwindings 564 and 566 in parallel and so that when the external alternating current source has a second predetermined nominal voltage rating, such as 220 VAC, the switch means 568 is positioned to connect the subwindings 564 and 566 in series.

With the switch means 568 in the appropriate position for the respective external alternating current source, the external source is applied to the transformer 562. The output from the transformer 562 is rectified by a rectifier circuit 570 so that a substantially direct current source is obtained for use by the remainder of the control means circuit.

It is to be noted that in FIGS. 5-7 a number of specific component values are disclosed. These values are shown for the purpose of fully disclosing a preferred embodiment of the control means represented thereby. These values are not to be considered as limiting the nature of the components, or of their values, encompassed by the scope of the present invention.

With reference again generally to FIGS. 5-7, the operation of the control means of the present invention will be described. First, the speed at which the motor is to be operated is selected by placing the switch means 534 and 538 in their appropriate positions. In the preferred embodiment any one of the three speed reference levels of 300 revolutions per minute, 600 revolutions per minute, or 900 revolutions per minute may be selected. Once this selection has been made, the power supply is connected to one terminal of the motor 100 by closing an on-off switch 572 (see FIG. 4 for its relative mounting location). When the switch 572 is initially closed, the output of the element 530 is at ground potential so the motor is energized to rotate the drive shaft 104.

As the shaft 104 rotates, so does the rotatable member 512. Because of the alternatingly disposed light-passing and light-occluding elements of the rotatable member 512, a series of electrical pulses is provided by the generating means 514 as the light from the light emitting diode 516 is alternatingly passed to and blocked from the photosensitive transistor 518 by the elements of the rotatable member 512.

This series of electrical pulses is applied to the activating and deactivating means 502 so that the series can be converted by the resistor-capacitor network 534 and the resistor network 536 into related first and second electrical signals for inputting into the comparing means 530. The comparing means 530 compares the signals and provides a third electrical signal at its output for activating or deactivating the motor 100. For example, in the preferred embodiment shown in the figures, the output of the element 530 is a pulse-width modulated signal. Thus, the motor 100 is shut-off for variable lengths of time depending upon the width of the high logic level pulses provided at the output of the element 530. When the output is at a low logic level, the motor 100 is energized to rotate the drive shaft 104.

Additionally, the output of the element 530 is applied to the indicator output adjusting means 504. As the output of the element 530 changes from a high logic level to a low logic level (i.e., as the motor is switched from an "off" condition to an "on" condition) the indicator activation control timer 552 generates a pulse which illuminates the indicator means 550. The adjusting means 504 is so constructed that when the motor 100 is rotating at the nominal speed as set by the switch means 534 and 538, the indicator means 550 is illuminated at a maximum brilliance. However, when the motor 100 is rotating at a speed other than the selected nominal speed, the pulse-width modulated signal provided by the element 530 causes the indicator means 550 to be relatively less intensely illuminated. In this way of controlling the magnitude of illumination in response to the speed of the motor drive shaft, the indicator means 550 indicates the relative speed of rotation of the drive shaft 104 for any one of the settings of the second switch means 538.

Furthermore, once the switch 572 has been closed to commence the operation of the motor 100 as previously described, if at any time thereafter, but prior to the opening of the switch 572, should the drive shaft 104 become jammed or otherwise prevented from rotating, the element 548 will detect this zero rotational speed and cause the output of the element 530 to deactivate the motor 100. This protects the motor whenever the drive shaft stalls.

Throughout this operation of the motor and motor speed control means, the power for effecting this operation may be provided by the internal direct current source 74. Alternatively, the power may be provided by either an external direct current source or an external alternating current source which is appropriately connected to the respective inputs of the power supply circuit 506.

Through this operation of the previously described control means, the speed of rotation of the drive shaft 104 of the motor 100 is initially selected from one of a plurality of speed reference levels and then maintained at that selected level.

The dimension of the bob 116 and the sleeve 112 are similar to those disclosed in U.S. Pat. No. 2,703,006 to Savins, so that the equations disclosed in Savins are applicable thereby providing an indicator dial 136 which will give a direct reading of the plastic viscosity, Newtonian viscosity, apparent viscosity, the yield point and the gel strength of the test fluid.

The viscometer 10 of the present invention is generally operated in the following manner. The viscometer 10 is utilized with a cup 200, shown in phantom lines in FIG. 1, which is set on the base 12 below rotating sleeve 112. The cup is filled with drilling mud or other fluid to be tested and the sleeve 112 is lowered into the cup of test fluid by adjusting the height of support leg 16.

The three position speed selector switch 539 is used to determine the speed of rotation of sleeve 112 as previously described. To determine the plastic viscosity and yield point of the test fluid, the speed selector switch 539 is set at its middle position so as to rotate the sleeve 112 at 600 rpm. When the indicator dial 136 stabilizes, a reading is taken therefrom. The time required for the dial 136 to stabilize depends upon the characteristics of the fluid being tested, as will be understood by those skilled in the art. Then the speed selector switch is moved to the low speed setting so as to turn the sleeve 112 at 300 rpm. Again, after the dial 136 stabilizes, a second reading is taken therefrom.

To determine the plastic viscosity in centipoises the 300 rpm reading is subtracted from the 600 rpm reading. The yield point in pounds per 100 sq. feet is equal to the 300 rpm reading minus the plastic viscosity. The Newtonian viscosity in centipoises is equal to the 300 rpm reading. The apparent viscosity in centipoises is the 600 rpm reading divided by two.

To determine the gel strength of the fluid, the speed selector switch is set at the high speed setting so that the sleeve 112 is rotated at 900 rpm until the test fluid is thoroughly mixed, then the test fluid is allowed to rest for 10 seconds. Then the motor shaft knob 105, which may also be referred to as the gel knob, is manually rotated at a speed of 3 rpm. The maximum reading on indicator dial 136 is the initial gel strength in pounds per 100 sq. feet.

Thus, the viscometer of the present invention is well adapted to attain the ends and advantages mentioned as well as those inherent therein. While presently preferred embodiments of the invention have been described for the purpose of this disclosure, numerous changes in the construction and arrangement of parts can be made by those skilled in the art, which changes are encompassed within the spirit of this invention as defined by the appended claims.

What is claimed is:

1. A viscometer comprising:
a base;
a housing;
a rotatable tubular sleeve extending downwardly from said housing;
support means for supporting said housing from said base, including one and only one support leg, adjustment means for adjusting a length of said support leg to vary a distance between said tubular sleeve and said base, and alignment means for maintaining said tubular sleeve over a fixed position on said base;
drive means for rotating said sleeve, including an electric motor, a toothed drive pulley attached to said motor, a toothed driven pulley connected to said rotatable tubular sleeve, and a resilient toothed endless belt engaging said drive pulley and said driven pulley;
a cylindrical non-metallic bob concentrically positioned within said tubular sleeve;
a bob shaft having a lower end connected to said bob and an upper end received in said housing;
torsional spring means connected between said bob shaft and said housing; and
indicator means for measuring a rotational deflection of said bob.

2. The viscometer of claim 1, wherein:
said support leg includes an upper leg member and a lower leg member, one of said leg members being telescopingly received in the other of said leg members.

3. The viscometer of claim 2, wherein:
said adjustment means of said support means includes a releasable locking means for selectively fixing said upper leg member relative to said lower leg member and releasing said upper leg member from said lower leg member.

4. The viscometer of claim 3, wherein:
said alignment means of said support means includes a vertical slot disposed in one of said upper and lower leg members, and a pin attached to the other of said upper and lower leg members, said pin being slidingly received in said slot so as to allow longitudinal movement of said upper leg member relative to said lower leg member and to prevent relative rotational movement between said upper and lower leg members.

5. The viscometer of claim 3, wherein:
said upper leg member is telescopingly received in said lower leg member; and
said releasable locking means includes:
packing gland means for wedging between said upper and lower leg members to prevent relative movement therebetween; and
collar means threadedly connected to an upper end of said lower leg member and including a radially inward projecting shoulder for engaging said packing gland means so that said upper and lower leg members may be locked together by tightening said collar means to wedge said packing gland means between said upper and lower leg members.

6. The viscometer of claim 2, wherein:
said support means further includes spring biasing means for biasing said telescoping upper and lower leg members toward an extended position.

7. The viscometer of claim 2, wherein:
said alignment means of said support means includes a vertical slot disposed in one of said upper and lower leg members, and a pin attached to the other of said upper and lower leg members, said pin being slidingly received in said slot so as to allow longitudinal movement of said upper leg member relative to said lower leg member and to prevent relative rotational movement between said upper and lower leg members.

8. The viscometer of claim 1, wherein:
said endless belt is further characterized as being constructed of urethane.

9. The viscometer of claim 1, further comprising:
a plastic cover means for snapping over an annular shoulder of a top cover of said housing to cover a calibration knob connected to said torsional spring means.

10. The viscometer of claim 1, further comprising:
a means for controlling the speed of rotation of a drive shaft of said electric motor, including:
a rotatable member connected to the drive shaft of the motor, said rotatable member having a plurality of alternatingly disposed light-passing and light-occluding elements;
means for generating a series of electrical pulses in response to the rotation of said rotatable member, said pulse generating means having a light-transmitting element and a light-receiving element disposed on opposite sides of said rotatable member so that the light-passing and light-occluding elements pass between the light-transmitting element and the light-receiving element as the rotatable member rotates; and
means, responsive to the series of electrical pulses, for alternatingly activating and deactivating the motor so that the speed of the drive shaft thereof is controlled.

11. The viscometer of claim 10, wherein:

said activating and deactivating means includes means, responsive to the cessation of the generation of the series of electrical pulses by said generating means, for stopping the activation of the motor.

12. The viscometer of claim 1, further comprising:
a means for variably setting the speed of rotation of a drive shaft of said motor, including:
means for detecting the speed of rotation of the drive shaft and for converting the speed into a proportional electrical signal;
a resistor-capacitor network having a first switch means for interconnecting respective ones of the resistor-capacitor components in a respective one of a plurality of combinations for establishing a first electrical comparison signal related to the proportional electrical signal;
a resistor network having a second switch means for selecting, in correspondence with the respective one of the plurality of resistor-capacitor combinations interconnected by the first switch means, a respective one of the resistors within said resistor network for providing a second electrical comparison signal related to the proportional signal; and
means for comparing the first and second electrical comparison signals and for providing an electrical motor speed control signal related to the comparison of the first and second electrical comparison.

13. The viscometer of claim 12, further comprising:
means, responsive to the electrical motor speed control signal provided by said comparing means, for adjusting the magnitude of the output of a means for indicating the relative speed of rotation of the drive shaft for any one setting of the second switch means.

14. The viscometer of claim 1, further comprising:
a means for controlling the speed of rotation of a drive shaft of said motor, including:
means for detecting the speed of rotation of the drive shaft;
means for comparing the detected speed of rotation to a selected one of a plurality of speed reference levels and for altering the speed of rotation in correspondence with the comparison of the detected speed and the selected reference level; and
a power supply circuit connected to said detecting means and said comparing and altering means, said power supply circuit including an internal direct current source.

15. A viscometer comprising:
a base;
a housing;
a rotatable tubular sleeve extending downwardly from said housing;
support means for supporting said housing from said base;
drive means having a drive shaft for rotating said sleeve;
a cylindrical bob concentrically positioned within said tubular sleeve;
a bob shaft having a lower end connected to said bob and an upper end received in said housing;
torsional spring means connected between said bob shaft and said housing;
means for measuring a rotational deflection of said bob;
a rotatable member connected to the drive shaft of said drive means, said rotatable member having a plurality of alternatingly disposed light-passing and light-occluding elements;
means for generating a series of electrical pulses in response to the rotation of said rotatable member, said pulse generating means having a light-transmitting element and a light-receiving element disposed on opposite sides of said rotatable member so that the light-passing and light-occluding elements pass between the light-transmitting element and the light-receiving element as the rotatable member rotates; and
means, responsive to the series of electrical pulses, for alternatingly activating and deactivating said drive means so that the speed of the drive shaft thereof is controlled, said activating and deactivating means including:
means for comparing the magnitudes of first and second electrical signals related to the series of electrical pulses and for providing a third electrical signal proportional to the comparison of the first and second signals;
a resistor-capacitor network switchably connected to a first input of said comparing means, said resistor-capacitor network having a first switch means for interconnecting the resistor-capacitor components into a selectable one of a plurality of combinations so that the first electrical signal related to the series of electrical pulses is thereby established; and
a resistor network having a second switch means for connecting respective ones of the resistors in said resistor network to a second input of said comparing means to thereby establish the second electrical signal related to the series of electrical pulses so that the nominal speed at which said drive means is to be operated can thereby be varied.

16. The viscometer as recited in claim 15, further comprising means, responsive to the third electrical signal provided by said comparing means, for adjusting the magnitude of the output of a means for indicating the relative speed of rotation of the drive shaft for any one setting of the second switch means.

17. The viscometer as recited in claim 16, further comprising a power supply circuit connected to said generating means, said activating and deactivating means, and said adjusting means, said power supply circuit including an internal direct current source.

18. The viscometer as recited in claim 17, wherein said power supply circuit further includes:
means for connecting an external direct current source to said power supply circuit; and
means for connecting an external alternating current source to said power supply circuit, said alternating current connecting means including:
a transformer having a primary winding comprised of two subwindings; and
means for connecting said two subwindings in parallel when the external alternating current source has a first predetermined nominal voltage rating and for connecting said two subwindings in series when the external alternating current source has a second predetermined nominal voltage rating.

19. A viscometer comprising:
a base;

a housing;

a rotatable tubular sleeve extending downwardly from said housing;

support means for supporting said housing from said base;

drive means having a drive shaft for rotating said sleeve;

a cylindrical bob concentrically positioned within said tubular sleeve;

a bob shaft having a lower end connected to said bob and an upper end received in said housing;

torsional spring means connected between said bob shaft and said housing;

means for measuring a rotational deflection of said bob;

a rotatable member connected to the drive shaft of said drive means, said rotatable member having a plurality of alternatingly disposed light-passing and light-occluding elements;

means for generating a series of electrical pulses in response to the rotation of said rotatable member, said pulse generating means having a light-transmitting element and a light-receiving element disposed on opposite sides of said rotatable member so that the light-passing and light-occluding elements pass between the light-transmitting element and the light-receiving element as the rotatable member rotates; and means, responsive to the series of electrical pulses, for alternatingly activating and deactivating said drive means so that the speed of the drive shaft thereof is controlled, said activating and deactivating means including means, responsive to the cessation of the generation of the series of electrical pulses by said generating means, for stopping the activation of said drive means.

20. A viscometer comprising:

a base;

a housing;

a rotatable tubular sleeve extending downwardly from said housing;

support means for supporting said housing from said base;

drive means having a drive shaft for rotating said sleeve;

a cylindrical bob concentrically positioned within said tubular sleeve;

a bob shaft having a lower end connected to said bob and an upper end received in said housing;

torsional spring means connected between said bob shaft and said housing;

means for measuring a rotational deflection of said bob;

means for detecting the speed of rotation of the drive shaft and for converting the speed into a proportional electrical signal;

a resistor-capacitor network having a first switch means for interconnecting respective ones of the resistor-capacitor components in a respective one of a plurality of combinations for establishing a first electrical comparison signal related to the proportional electrical signal;

a resistor network having a second switch means for selecting, in correspondence with the respective one of the plurality of resistor-capacitor combinations interconnected by the first switch means, a respective one of the resistors within said resistor network for providing a second electrical comparison signal related to the proportional signal; and means for comparing the first and second electrical comparison signals and for providing an electrical drive means speed control signal related to the comparison of the first and second electrical comparison signals.

21. The viscometer as recited in claim 20, further comprising means, responsive to the electrical drive means speed control signal provided by said comparing means, for adjusting the magnitude of the output of a means for indicating the relative speed of rotation of the drive shaft for any one setting of the second switch means.

22. The viscometer as recited in claim 20, further comprising a power supply circuit connected to said detecting means and said comparing means, said power supply circuit including an internal direct current source.

23. The viscometer as recited in claim 22, wherein said power supply circuit further includes:

means for connecting an external direct current source to said power supply circuit; and means for connecting an external alternating current source to said power supply circuit, said alternating current connecting means including:

a transformer having a primary winding comprised of two subwindings; and means for connecting said two subwindings in parallel when the external alternating current source has a first predetermined nominal voltage rating and for connecting said two subwindings in series when the external alternating current source has a second predetermined nominal voltage rating.

24. The viscometer as recited in claim 23, further comprising means, responsive to the drive means speed control signal provided by said comparing means, for adjusting the magnitude of the output of a means for indicating the relative speed of rotation of the drive shaft for any one setting of the second switch means.

25. A viscometer as recited in claim 20, further comprising means, responsive to the absence of the proportional electrical signal, for stopping the activation of said drive means.

26. In combination with a viscometer apparatus of the type having a base, a housing, a support means for supporting said housing from said base, a rotatable tubular sleeve extending downwardly from said housing, means for rotating said sleeve, a cylindrical bob positioned with respect to said sleeve such that rotation of said sleeve within a liquid will rotate said liquid and thereby impart viscous drag to said bob, means including a spring for imparting a torque to said bob proportional to the deflection of said bob from a zero position, and means for measuring the deflection of said bob from said zero position, the improvement which comprises:

said support means including one and only one support leg connected between said base and said housing and arranged such that a longitudinal axis of said support leg is parallel to and horizontally spaced from an axis of rotation of said tubular sleeve, adjustment means for adjusting a length of said support leg to vary a distance between said tubular sleeve and said base, and alignment means for preventing rotation of said housing about said longitudinal axis of said support leg and for thereby maintaining said tubular sleeve over a fixed position on said base.

27. The apparatus of claim 26, wherein:
said support leg includes an upper leg member and a lower leg member, one of said leg members being telescopingly received in the other of said leg members.

28. The apparatus of claim 27, wherein:
said adjustment means includes a releasable locking means for selectively fixing said upper leg member relative to said lower leg member and releasing said upper leg member from said lower leg member.

29. The apparatus of claim 28, wherein:
said alignment means includes a vertical slot disposed in one of said upper and lower leg members, and a pin attached to the other of said upper and lower leg members, said pin being slidingly received in said slot so as to allow longitudinal movement of said upper leg member relative to said lower leg member and to prevent relative rotational movement between said upper and lower leg members.

30. The apparatus of claim 28, wherein:
said support means further includes spring biasing means for biasing said telescoping upper and lower leg members toward an extended position.

31. The apparatus of claim 28, wherein:
said alignment means includes a vertical slot disposed in one of said upper and lower leg members, and a pin attached to the other of said upper and lower leg members, said pin being slidingly received in said slot so as to allow longitudinal movement of said upper leg member relative to said lower leg member and to prevent relative rotational movement between said upper and lower leg members.

32. In combination with a viscometer apparatus of the type having a base, a housing, support means for supporting said housing from said base, a rotatable tubular sleeve extending downwardly from said housing, means for rotating said sleeve, a cylindrical bob positioned with respect to said sleeve such that rotation of said sleeve within a liquid will rotate said liquid and thereby impart viscous drag to said bob, means including a spring for imparting a torque to said bob proportional to the deflection of said bob from a zero position, and means for measuring the deflection of said bob from said zero position, the improvement wherein said support means comprises:
one and only one support leg, said support leg including an upper leg member telescopingly received in a lower leg member;
adjustment means for adjusting a length of said support leg to vary a distance between said tubular sleeve and said base, said adjustment means including a releasable locking means for selectively fixing said upper leg member relative to said lower leg member and releasing said upper leg member from said lower leg member, said releasable locking means including:
packing gland means for wedging between said upper and lower leg members to prevent relative movement therebetween; and
collar means threadedly connected to an upper end of said lower leg member and including a radially inward projecting shoulder for engaging said packing gland means so that said upper and lower leg members may be locked together by tightening said collar means to wedge said packing gland means between said upper and lower leg members; and
alignment means for maintaining said tubular sleeve over a fixed position on said base.

33. A method of testing a rheological property of a fluid, utilizing a viscometer of the type having a base, a housing, a rotatable tubular sleeve extending downwardly from said housing, support means for supporting said housing from said base, drive means for rotating said sleeve, a cylindrical bob concentrically positioned within said tubular sleeve, a bob shaft having a lower end connected to said bob and an upper end received in said housing, torsional spring means connected between said bob shaft and said housing, and indicator means for measuring a rotational deflection of said bob, said method comprising the steps of:
placing a sample of said fluid in a container upon the base below said tubular sleeve;
adjusting a length of said support means to lower said tubular sleeve into said fluid, said support means including:
one and only one support leg having a lower leg member and an upper leg member telescopingly received in said lower leg member;
packing gland means for wedging between said upper and lower leg members to prevent relative movement therebetween;
collar means threadedly connected to an upper end of said lower leg member and including a radially inward projecting shoulder for engaging said packing gland means so that said upper and lower leg members may be locked together by tightening said collar means to wedge said packing gland means between said upper and lower leg members; and
spring biasing means for biasing said telescoping upper and lower leg members toward an extended position;
wherein said step of adjusting a length of said support means includes the steps of:
compressing said spring biasing means to move said tubular sleeve downward into said fluid;
tightening said collar means; and
wedging said packing gland means between said upper and lower leg members to lock said leg members together; and
rotating said tubular sleeve with said drive means to test said fluid, said drive means including an electric motor, a toothed drive pulley attached to said motor, a toothed driven pulley connected to said rotatable tubular sleeve, and a resilient toothed endless belt engaging said drive pulley and said driven pulley.

34. The method of claim 33, wherein said step of rotating said tubular sleeve comprises the steps of:
rotating said toothed drive pulley;
driving said resilient toothed endless belt from said drive pulley; and
rotating said toothed driven pulley by driving engagement with said resilient toothed endless belt.

35. A method of controlling the speed of rotation at which a rheological property of a fluid is to be determined by a viscometer of the type having a base, a housing, a rotatable tubular sleeve extending downwardly from said housing, support means for supporting said housing from said base, drive means for rotating said sleeve, a cylindrical bob concentrically positioned within said tubular sleeve, a bob shaft having a lower end connected to said bob and an upper end received in said housing, torsional spring means connected between said bob shaft and said housing, and indicator means for measuring a rotational deflection of said bob, said method comprising the steps of:

connecting a rotatable member having a plurality of alternatingly disposed light-passing and light-occluding members to the drive shaft of said drive means;

selecting one of a plurality of resistor-capacitor combinations and a respective one of a plurality of variable resistors;

generating a series of electrical pulses in response to said rotatable member being rotated by said drive means between a light-transmitting element and a light-receiving element;

applying said series of electrical pulses to said selected one of said resistor-capacitor combinations to obtain a first comparison signal and to said selected one of said variable resistors to obtain a second comparison signal;

comparing said first comparison signal to said second comparison signal and obtaining a third signal therefrom;

transmitting said third signal to said drive means to periodically activate and deactivate said drive means so that the speed of said drive means is controlled; and deactivating said drive means when no series of electrical pulses is generated.

36. The method of claim 35, further comprising the step of:

utilizing a power supply circuit having an internal direct current source, an external direct current source connecting means, and an external alternating source connecting means to energize an electronic circuit for performing said steps of generating, applying, comparing, transmitting and deactivating.

* * * * *

UNITED STATES PATENT AND TRADEMARK OFFICE
CERTIFICATE OF CORRECTION

PATENT NO. : 4,299,118
DATED : November 10, 1981
INVENTOR(S) : Gau et al

It is certified that error appears in the above-identified patent and that said Letters Patent is hereby corrected as shown below:

On the title page Assignee should read

--(73) Assignee: Halliburton Company --

Signed and Sealed this

Twenty-sixth Day of March 1985

[SEAL]

Attest:

DONALD J. QUIGG

Attesting Officer

Acting Commissioner of Patents and Trademarks